United States Patent
Matsushita et al.

(10) Patent No.: US 7,879,789 B2
(45) Date of Patent: Feb. 1, 2011

(54) SURFACTANT AND COMPOSITION CONTAINING THE SAME

(75) Inventors: Yuji Matsushita, Yokohama (JP); Takashi Ohmori, Yokohama (JP); Akira Noda, Yokohama (JP)

(73) Assignee: Shiseido Company Ltd., Chou-ku, Tokyo (JP)

( * ) Notice: Subject to any disclaimer, the term of this patent is extended or adjusted under 35 U.S.C. 154(b) by 0 days.

(21) Appl. No.: 12/302,522

(22) PCT Filed: May 14, 2007

(86) PCT No.: PCT/JP2007/059855
§ 371 (c)(1), (2), (4) Date: Nov. 26, 2008

(87) PCT Pub. No.: WO2007/138847
PCT Pub. Date: Dec. 6, 2007

(65) Prior Publication Data
US 2009/0186791 A1  Jul. 23, 2009

(30) Foreign Application Priority Data

May 26, 2006  (JP) ............................ 2006-146268
May 26, 2006  (JP) ............................ 2006-146269

(51) Int. Cl.
*C11D 1/29* (2006.01)
*C11D 1/72* (2006.01)
*C11D 3/37* (2006.01)

(52) U.S. Cl. .................. 510/475; 510/130; 510/421; 510/426; 510/492; 510/524; 424/401; 424/70.11

(58) Field of Classification Search .............. 510/130, 510/421, 426, 475, 492, 524; 424/401, 70.11
See application file for complete search history.

(56) References Cited

U.S. PATENT DOCUMENTS 2,802,789 A * 8/1957 Stayner .................. 510/495
4,304,691 A * 12/1981 Farmer et al. ............ 510/125
5,167,872 A * 12/1992 Pancheri et al. .......... 510/237

FOREIGN PATENT DOCUMENTS

| JP | 9-67333 | 3/1997 |
| JP | 9-87289 | 3/1997 |
| JP | 2004-98054 | 4/2004 |
| WO | WO 98/51713 | * 11/1998 |

OTHER PUBLICATIONS

Engelhard et al, "Improvement In The Dyeability Of Acrylonitrile Polymers", Apr. 25, 1970, Die Angewandte Malcromolelculare Chemie 14 (1970) 1-24 (Nr.186), pp. 1-24.*
English Abstarct of Engelhard et al, "Improvement In The Dyeability Of Acrylonitrile Polymers", Apr. 25, 1970, Die Angewandte Malcromolelculare Chemie 14 (1970) 1-24 (Nr.186), pp. 101-102.*
International Search Report for PCT/JP2007/059855 mailed Jun. 12, 2007, two pages.
Japanese Patent Abstract Publication No. 09-067333 published Mar. 11, 1997, 37 pages.
Japanese Patent Abstract Publication No. 09-087289 published Mar. 31, 1997, 37 pages.
Japanese Patent Abstract Publication No. 2004-098054 published Apr. 2, 2004, 19 pages.

* cited by examiner

*Primary Examiner*—Brian P Mruk
(74) *Attorney, Agent, or Firm*—Rankin, Hill & Clark LLP

(57) ABSTRACT

The present invention is to provide a new surfactant that can be used as an emulsifier excellent in emulsion stability and texture in use and as a cleanser excellent in cleansing power and texture in use and having low skin irritation. A surfactant consisting of a compound represented by the below-described general formula (1).

$$Y\text{—}O\text{-}(EO)_l\text{-}(AO)_m\text{-}(EO)_n\text{-}X \qquad (1)$$

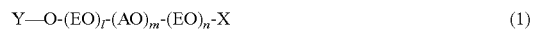

(In the formula, AO represents an oxyalkylene group having 3 to 4 carbon atoms; m is the average addition mole number of the oxyalkylene group and satisfies $5 \leqq m \leqq 100$. EO represents an oxyethylene group; l and n are the average addition mole numbers of the oxyethylene groups and satisfy $0 \leqq l \leqq 4$ and $0 \leqq n \leqq 4$. Either X or Y or both are a functional group represented by —$SO_3M$, —$COOM$, —$HPO_3M$, —$(CH_2)_q$—$SO_3M$, or —$(CH_2)_q$—COO, wherein M is a hydrogen ion or a monovalent inorganic or organic cation, and q is the number of carbon atoms of the linked alkylene group and satisfies $1 \leqq q \leqq 4$. When either X or Y is the above-described functional group, the other one can be a hydrogen atom, a methyl group, or an ethyl group.)

7 Claims, No Drawings

SURFACTANT AND COMPOSITION CONTAINING THE SAME

RELATED APPLICATIONS

This application claims the priority of Japanese Patent Application No. 2006-146268 filed on May 26, 2006, and the Japanese Patent Application No. 2006-146269 filed on May 26, 2006, which is incorporated herein by reference.

TECHNICAL FIELD

The present invention relates to surfactants and compositions containing the same, and in particular, relates to the development of new surfactants usable as the emulsifier excellent in emulsion stability and texture in use and as a cleanser excellent in cleansing power and texture in use and having low skin irritation.

BACKGROUND ART

Traditionally, a surfactant is blended in emulsion-type skin external preparations, such as cream and milky lotion, as an emulsifier; a surfactant is also blended in cleanser compositions, such as shampoo and body shampoo, as a cleanser. A surfactant has a hydrophilic group and a hydrophobic group in the molecule, and there are numerous surfactants depending on their combination, and there are various applications depending on the intended use. If we classify surfactants by focusing on the hydrophilic group, they can be classified into ionic surfactants, which dissociate into ions when dissolved in water, and nonionic surfactants, which do not dissociate into ions. Among these, the ionic surfactants are classified into anionic surfactants, cationic surfactants, and amphoteric surfactants depending on the charge generated by dissociation. On the other hand, if we focus on the hydrophobic group, linear or branched hydrocarbon surfactants, fluorosurfactants, silicone surfactants, etc. can be listed; however, widely used surfactants are hydrocarbon surfactants.

Anionic hydrocarbon surfactants exhibit an excellent foaming property, cleansing power, dispersing power, and emulsifying power. However, many of them have high Kraft points, and they cannot satisfactorily perform below the Kraft temperature. Among anionic hydrocarbon surfactants, most widely used sulfate-type surfactants have high foaming property. However, they may exhibit skin and eye irritation. In order to alleviate the irritation, alkyl-ether anionic surfactants, in which a polyoxyethylene group is inserted between the hydrocarbon group and the anionic group, are also used. However, the above-described problems have not been satisfactorily solved. For the reduction of skin and eye irritation, a means for achieving a high-molecular weight and a means for combining with an amphoteric surfactant are commonly known. In this case, however, there are occasions in which the surfactant capability and the texture in use are lowered. In addition, carboxylate-type surfactants are also known; however, the cleansing properties and texture in use are poor.

On the other hand, high-molecular nonionic surfactants containing a polyoxyalkylene group as the hydrophobic domain have been known. For example, Pluronic surfactants, which are triblock copolymers of ethylene oxide and propylene oxide, have been widely used because they have low irritability and low toxicity. However, it is necessary to blend a large amount of the surfactant for the fulfillment of the function, and there has been a problem in that a sticky feeling is generated as texture in use.

DISCLOSURE OF THE INVENTION

Problem to be Solved by the Invention

The present invention was made in view of the above-described problems, and the object of the present invention is to provide a new surfactant that can be used as an emulsifier excellent in emulsion stability and texture in use and as a cleanser excellent in cleansing power and texture in use and having low skin irritation.

Means to Solve the Problem

The present inventors have diligently studied in view of the above-described problems. As a result, the present inventors have found that a compound obtained by the introduction of an anionic functional group, such as an alkylsulfonate group or a sulfate ester group, at the terminal of a compound having a hydrophobic polyoxyalkylene group can be used as an emulsifier excellent in emulsion stability and texture in use. In addition, the present inventors have found that the compound thus obtained can be used as a cleanser excellent in cleansing power and texture in use and having low skin irritation, thus leading to completion of the present invention.

Thus, the surfactant of the present invention is characterized in that the surfactant is a compound represented by the following general formula (1).

$$Y\text{—}O\text{-}(EO)_l\text{-}(AO)_m\text{-}(EO)_n\text{-}X \qquad (1)$$

(In the formula, AO represents an oxyalkylene group having 3 to 4 carbon atoms; m is the average addition mole number of the oxyalkylene group and satisfies $5 \leq m \leq 100$. EO represents an oxyethylene group; l and n are the average addition mole numbers of the oxyethylene groups and satisfy $0 \leq l \leq 4$ and $0 \leq n \leq 4$. Either X or Y or both are a functional group represented by —SO$_3$M, —COOM, —HPO$_3$M, —(CH$_2$)$_q$—SO$_3$M, or —(CH$_2$)$_q$—COOM, wherein M is a hydrogen ion or a monovalent inorganic or organic cation, and q is the number of carbon atoms of the linked alkylene group and satisfies $1 \leq q \leq 4$. When either X or Y is the above-described functional group, the other one can be a hydrogen atom, a methyl group, or an ethyl group.)

The emulsifier of the present invention is characterized in that the emulsifier consists of the above-described surfactant.

Furthermore, the skin external composition of the present invention is characterized in that the skin external composition contains one or more emulsifiers described above. Furthermore, it is preferable that the skin external composition contains 0.001 to 10 mass % of the above-described emulsifier.

The cleanser of the present invention is characterized in that the cleanser consists of the above-described surfactant.

Furthermore, the cleanser composition of the present invention is characterized in that the cleanser composition contains one or more cleansers described above. Furthermore, it is preferable that the cleanser composition contains 0.1 to 60 mass % of the above-described cleanser.

Effect of the Invention

The surfactant of the present invention can be used as an emulsifier or cleanser. When the surfactant of the present invention is used as an emulsifier, it is excellent in emulsion stability and texture in use. Furthermore, when the surfactant of the present invention is used as a cleanser, it is excellent in cleansing power and texture in use, and the skin irritation is also low.

BEST MODE FOR CARRYING OUT THE INVENTION

In the following section, the preferable mode for carrying out the present invention is described.

The surfactant of the present invention is a compound represented by the following general formula (1).

$$Y-O-(EO)_l-(AO)_m-(EO)_n-X \quad (1)$$

AO is an oxyalkylene group having 3 to 4 carbon atoms, and it is the hydrophobic domain in the compound of the present invention. Examples of AO include an oxypropylene group, oxyisopropylene group, oxybutylene group, oxyisobutylene group, and oxy-t-butylene group. The configuration can be a copolymer in which two or more oxyalkylene groups having 3 to 4 carbon atoms are contained in a compound. In this case, the polymerization of different oxyalkylene groups can be either block-type or random-type. If AO is an oxyalkylene group having 5 or more carbon atoms, it is difficult to obtain a high purity derivative. The average addition mole number of AO, which is represented by m, should be 5 to 100, and preferably 10 to 50. If m is less than 5, the surfactant will have low hydrophobicity and will not show enough surface activity. If m exceeds 100, the preparation of the compound will become difficult. Furthermore, it is especially desirable for AO that the percentage of oxyalkylene groups having 4 carbon atoms, which can provide stronger hydrophobicity, is high from the standpoint of emulsion stability and cleansing properties. The percentage of oxyalkylene groups having 4 carbon atoms with respect to the sum of AO is preferably 50 mass % or higher, and more preferably 90 mass % or higher.

EO is an oxyethylene group having 2 carbon atoms. The compound of the present invention can be a copolymer in which oxyethylene groups are added as well as the above-described oxyalkylene groups. The average addition mole numbers of the oxyethylene groups, represented by l and n, are 0 to 4. If the percentage of the oxyethylene groups is too high, the surfactant will have low hydrophobicity and will not show enough surface activity. The percentage of the oxyalkylene groups having 3 to 4 carbon atoms with respect to the sum of the oxyalkylene groups having 3 to 4 carbon atoms and the oxyethylene groups should be 50 mass % or higher, and more preferably 90 mass % or higher.

Either X or Y or both are a hydrophilic anionic substituent group represented by $-SO_3M$, $-COOM$, $-HPO_3M$, $-(CH_2)_q-SO_3M$, or $-(CH_2)_q-COOM$. Here, M is a hydrogen ion, or a monovalent inorganic or organic cation. Examples of monovalent inorganic cations include sodium, potassium, and lithium ions, and the examples of monovalent organic cations include ammonium, monoethanolammonium, and triethanolammonium ions. Furthermore, q is the number of carbon atoms of the linked alkylene group and satisfies $1 \leq q \leq 4$.

Both X and Y can be the above-described anionic substituent groups. When one of them is the above-described anionic substituent group, the other one can be a hydrogen atom, methyl group, or ethyl group. For example, when $-SO_3Na$ is substituted at the terminal of a oxyalkylene compound having hydrogen atoms at both terminals, both X and Y are $-SO_3Na$ in the both-terminal-substituted compound, and X (or Y) is $-SO_3Na$ in the one-terminal-substituted compound and Y (or X) is a hydrogen atom. As the surfactant of the present invention, a mixture of both-terminal-substituted compound and the one-terminal-substituted compound may be used.

Furthermore, the hydrophilic-lipophilic balance of a compound can be adjusted by varying the average addition mole number, m, of oxyalkylene groups having 3 to 4 carbon atoms and by varying the species of X and Y; thus the hydrophilic-lipophilic balance can be suitably adjusted depending on the specific intended use.

The surfactant of the present invention can be prepared by publicly known methods. Examples of production methods include a method in which the above-described anionic substituent group is introduced to a polyoxyalkylene compound containing the above-described AO (or also containing the above-described EO), or a method in which other alkylene oxide or alkylene glycol is addition-polymerized to an alkylene oxide or alkylene glycol having an anionic substituent group.

The polyoxyalkylene compound used as a raw material is not limited in particular. For example, the polyoxyalkylene compound can be obtained by the homopolymerization of propylene oxide, propylene glycol, butylene oxide, butylene glycol, etc. or the copolymerization of two kinds or more. Furthermore, a commercial product may be used as the polyoxyalkylene compound. For example, Uniol (product of NOF Co., Ltd.) and Newpol (product of Sanyo Chemical Industries, Ltd.) are available. If necessary, the polyoxyalkylene compound may be reacted with an alkyl (alkenyl) halide in the presence of an alkaline catalyst for the alkyl (alkenyl) etherification of the terminal of the oxyalkylene group. Examples of alkyl (alkenyl) halides include methyl chloride, ethyl chloride, propyl chloride, butyl chloride, vinyl chloride, allyl chloride, methyl bromide, ethyl bromide, methyl iodide, and ethyl iodide. The amount of loaded alkyl halide is generally 100 to 400 mole % with respect to the number of reacting hydroxyl groups.

The introduction of an anionic substituent group to the polyoxyalkylene compound can be achieved by following the introduction method of an anionic substituent group to an aliphatic alcohol (widely known as a production method of anionic hydrocarbon surfactants). The substitution compound with introduced $-SO_3M$, as an anionic substituent group, can be obtained by the sulfation of the polyoxyalkylene compound with, for example, chlorosulfonic acid, sulfuric anhydride, fuming sulfuric acid, or sulfamic acid. The $-COOM$-substituted compound can be obtained by the reaction of, for example, the polyoxyalkylene compound and sodium monochloroformate under basic conditions. The $-HPO_3M$-substituted compound can be obtained by the phosphorylation of the polyoxyalkylene compound with, for example, phosphoric anhydride, polyphosphoric acid, or oxychlorophosphoric acid. The $-(CH_2)_q-SO_3M$-substituted compound can be obtained by the reaction of, for example, the polyoxyalkylene compound and 1,3-propane sultone under basic conditions. The $-(CH_2)_q-COOM$-substituted compound can be obtained by the reaction of, for example, the polyoxyalkylene compound and sodium monochloroacetate under basic conditions.

When an anionic substituent group is introduced in the polyoxyalkylene compound, a compound in which the anionic substituent group is added on only one terminal of the polyoxyalkylene compound, a compound in which the anionic substituent group is added on both terminals, or a mixture thereof may be prepared depending on reaction conditions. Respective single compounds or a mixture thereof can be used by applying a purification process, as necessary.

A skin external composition excellent in emulsion stability and texture in use can be obtained by using the thus prepared surfactant of the present invention as the emulsifier. In the skin external composition of the present invention, the blending quantity of the emulsifier is preferably 0.001 to 10 mass %, and most preferably 0.01 to 5 mass percent. If the blending quantity of the emulsifier is less than 0.001 mass %, the effect of the emulsifier cannot be produced. Even if the blending quantity of the emulsifier exceeds 10 mass %, the higher effect cannot be expected, and a sticky feeling due to the emulsifier is generated.

In the skin external composition of the present invention, so far as the effect of the present invention is not undermined, various components such as powder components, liquid fat, solid fat, wax, hydrocarbons, higher fatty acids, higher alcohols, anionic surfactants, cationic surfactants, amphoteric surfactants, nonionic surfactants, moisturizers, water-soluble polymers, thickeners, metal ion sequestering agents, lower alcohols, polyhydric alcohols, saccharides, amino acids, organic amines, polymer emulsions, pigments, pH adjusters, skin nutrients, vitamins, preservatives, antioxidants, antioxidant promoters, perfumes, and water can be suitably blended, as necessary, and normal preparation methods can be used in accordance with desired product forms. In addition, in the skin external composition of the present invention, other emulsifiers (surfactants) may be used in combination with the emulsifier of the present invention.

In addition, the cleanser composition excellent in cleansing power and texture in use and having low skin irritation can be obtained by using the surfactant of the present invention as the cleanser. In the cleanser composition of the present invention, the blending quantity of the cleanser is preferably 0.1 to 60 mass %, and most preferably 1 to 30 mass %. If the blending quantity of the cleanser is less than 0.1 mass %, the effect of the cleanser cannot be produced. Even if the blending quantity of the cleanser exceeds 60 mass %, the higher effect cannot be expected, and a sticky feeling due to the cleanser is generated.

In the cleanser composition of the present invention, so far as the effect of the present invention is not undermined, various components such as powder components, liquid fat, solid fat, wax, hydrocarbons, higher fatty acids, higher alcohols, anionic surfactants, cationic surfactants, amphoteric surfactants, nonionic surfactants, moisturizers, water-soluble polymers, thickeners, metal ion sequestering agents, lower alcohols, polyhydric alcohols, saccharides, amino acids, organic amines, polymer emulsions, pigments, pH adjusters, skin nutrients, vitamins, preservatives, antioxidants, antioxidant promoters, perfumes, and water can be suitably blended, as necessary, and normal preparation methods can be used in accordance with desired product forms. In addition, in the cleanser composition of the present invention, other surfactants may be used in combination with the cleanser of the present invention.

EXAMPLE 1

Hereinafter, the present invention will be described in more detail with reference to examples; however, the present invention is not limited by these examples. Initially, the synthesis methods of the surfactants of the present invention will be described.

Synthesis Example 1

Sodium Polyoxybutyl (Average Molecular Weight 700) Propanesulfonate

To 5 g of polybutylene glycol with average molecular weight 700 (Uniol PB-700, product of Nippon Oil & Fats Co., Ltd.), 1.24 g of 1,3-propane sultone was added, and the mixture was stirred for 2 hours at 100° C. The solution was returned to room temperature, 10 mL of 1 N sodium hydrogencarbonate aqueous solution was added, and the stirring was continued for 15 minutes. Ethanol was added to the solution, the precipitated salt was removed by filtration, and ethanol/water was distilled away under reduced pressure. The residue was purified by separation with silica gel chromatography (chloroform:methanol=6:1), and 0.5 g of liquid light-yellow sodium polyoxybutylene (MW=700) propanesulfonate was obtained. The nuclear magnetic resonance spectral (NMR) data and infrared spectrum (IR) of the obtained compound were as follows, and it was confirmed to be the desired compound.

*Sodium Polyoxybutylene (Mw=700) Propanesulfonate
NMR (CD3OD, δ); 0.8-1.3 (m, —CH3, 27H), 1.4-1.7 (m, —CH2, 16H), 2.0 (m, —CH2, 2H), 2.9 (t, —CH2, 2H), 3.3-3.8 (—OCH2, —OCH, 27H)

Synthesis Example 2

Sodium Polyoxybutylene (Average Molecular Weight 700) Sulfate

Into 30 mL of chloroform, 20 g of polybutylene glycol with an average molecular weight of 700 (Uniol PB-700, product of Nippon Oil & Fats Co., Ltd.) was dissolved. While the solution was maintained at 10° C., argon gas was introduced, and 3.3 g of chlorosulfonic acid was slowly dropwise added to the solution. After the dropwise addition, the solution was returned to room temperature and stirred for 15 minutes, 60 mL of 1 N sodium hydrogencarbonate aqueous solution was added, and the stirring was continued for 15 minutes. Methanol was added to the cloudy solution, the precipitated salt was removed by filtration, and methanol/water was distilled away under reduced pressure. The residue was purified by separation with silica gel chromatography (chloroform:methanol=6:1), and 9.5 g of liquid colorless sodium salt of polyoxybutylene (MW=700) sulfated at one terminal and 2.4 g of liquid colorless sodium salt of polyoxybutylene (MW=700) sulfated at both terminals were obtained. The nuclear magnetic resonance spectral (NMR) data and infrared spectra (IR) of the obtained compounds were as follows, and they were confirmed to be the desired compounds.

*Sodium Polyoxybutylene (Mw=700) Sulfated at One Terminal
NMR (CD3OD, δ); 0.8-1.2 (m, —CH3, 27H), 1.3-1.9 (m, —CH2, 16H), 3.2-3.9 (—OCH2, —OCH, 26H), 4.3 (m, —OCH, 1H)
IR (neat) 3450, 2970, 2930, 2880, 1460, 1260, 1100 cm-1

*Sodium Polyoxybutylene (Mw=700) Sulfated at Both Terminals
NMR (CD3OD, δ); 0.8-1.2 (m, —CH3, 27H), 1.3-1.9 (m, —CH2, 16H), 3.2-3.9 (—OCH2, —OCH, 26H), 4.3 (m, —OCH, 2H)
IR (neat) 3450, 2970, 2930, 2880, 1460, 1260, 1100 cm-1

Synthesis Example 3

Sodium Polyoxybutylene (Average Molecular Weight 2000) Sulfate

Into 20 mL of chloroform, 20 g of polybutylene glycol with an average molecular weight of 2000 (Uniol PB-2000, product of Nippon Oil & Fats Co., Ltd.) was dissolved. While the solution was maintained at 10° C., argon gas was introduced, and 1.4 g of chlorosulfonic acid was slowly dropwise added to the solution. After the dropwise addition, the solution was returned to room temperature and stirred for 15 minutes, 30 mL of 1 N sodium hydrogencarbonate aqueous solution was added, and the stirring was continued for 15 minutes. Methanol was added to the cloudy solution, the precipitated salt was removed by filtration, and methanol/water was distilled away under reduced pressure. The residue was purified by separation with silica gel chromatography (chloroform:methanol=10:1), and 9.3 g of liquid colorless sodium salt of polyoxybutylene (MW=2000) sulfated at one terminal and 1.5 g of liquid colorless sodium salt of polyoxybutylene (MW=2000) sulfated at both terminals were obtained. The nuclear magnetic resonance spectral (NMR) data and infrared spectra (IR) of the obtained compounds were as follows, and they were confirmed to be the desired compounds.

*Sodium Polyoxybutylene (Mw=2000) Sulfated at One Terminal

NMR (CD3OD, δ); 0.8-1.2 (m, —CH3, 81H), 1.3-1.9 (m, —CH2, 52H), 3.2-3.9 (—OCH2, —OCH, 83H), 4.3 (m, —OCH, 1H)

IR (neat) 3470, 2960, 2930, 2880, 1460, 1260, 1100 cm-1

*Sodium Polyoxybutylene (Mw=2000) Sulfated at Both Terminals

NMR (CD3OD, δ); 0.8-1.2 (m, —CH3, 81H), 1.3-1.9 (m, —CH2, 52H), 3.2-3.9 (—OCH2, —OCH, 83H), 4.3 (m, —OCH, 2H)

IR (neat) 3470, 2960, 2930, 2880, 1460, 1260, 1100 cm-1

Synthesis Example 4

Sodium Polyoxypropylene (Average Molecular Weight 1000) Sulfate

Into 30 mL of chloroform, 30 g of polypropylene glycol with an average molecular weight of 1000 (Newpol PP-1000, product of Sanyo Chemical Industries, Ltd.) was dissolved. While the solution was maintained at 10° C., argon gas was introduced, and 4.2 g of chlorosulfonic acid was slowly dropwise added to the solution. After the dropwise addition, the solution was returned to room temperature and stirred for 15 minutes, 70 mL of 1 N sodium hydrogencarbonate aqueous solution was added, and the stirring was continued for 15 minutes. Methanol was added to the cloudy solution, the precipitated salt was removed by filtration, and methanol/water was distilled away under reduced pressure. The residue was purified by separation with silica gel chromatography (chloroform:methanol=10:1), and 9.8 g of liquid colorless sodium salt of polyoxypropylene (MW=1000) sulfated at one terminal and 2.8 g of liquid colorless sodium salt of polyoxypropylene (MW=1000) sulfated at both terminals were obtained. The nuclear magnetic resonance spectral (NMR) data and infrared spectra (IR) of the obtained compounds were as follows, and they were confirmed to be the desired compounds.

*Sodium Polyoxypropylene (Mw=1000) Sulfated at One Terminal

NMR (CD3OD, δ); 0.9-1.4 (m, —CH3, 39H), 3.5-3.9 (—OCH2, —OCH, 38H), 4.5 (m, —OCH, 2H)

IR (neat) 3470, 2960, 2930, 2880, 1460, 1260, 1100 cm-1

*Sodium Polyoxypropylene (Mw=1000) Sulfated at Both Terminals

NMR (CD3OD, δ); 0.9-1.4 (m, —CH3, 39H), 3.5-3.9 (—OCH2, —OCH, 38H), 4.5 (m, —OCH, 2H)

IR (neat) 3470, 2960, 2930, 2880, 1460, 1260, 1100 cm-1

The present inventors have prepared various polyoxyalkylene substitution compounds according to the respective synthesis examples and evaluated the emulsion stability for the blending compositions shown in Table 1. The evaluation results are shown in Table 2. The various evaluation items are as follows.

TABLE 1

|  | Components | Blending quantity (weight %) |
|---|---|---|
| Oil phase components | Squalane | 1 |
|  | Dimethylpolysiloxane (6 cs) | 1 |
| Water phase components | 1,3-Butylene glycol | 10 |
|  | Xanthan gum | 0.2 |
|  | Ion exchanged water | 86.8 |
| Emulsifier | Examples 1-1 to 1-6, Comparative Examples 1-1 to 1-3 | 1 |

"Emulsion Stability"

The oil phase component, water phase component, and various emulsifiers shown in Table 1 were mixed, and the emulsification mixing was carried out with a homomixer at 8000 rpm for 1 minute. The appearance was visually observed 30 minutes after emulsification, and the appearances were also observed after being stored for 3 days on standing at room temperature and also at −5° C., respectively. The evaluation criteria were as follows.

◯ . . . The emulsion was uniform and milky white.

Δ . . . A small amount of floating oil was observed; however, it was milky white.

X . . . Solid matter was observed, or the separation of the water phase and the oil phase was observed.

TABLE 2

|  |  | 30 minutes | 3 days | |
|---|---|---|---|---|
|  | Emulsifier | ambient temperature | ambient temperature | −5° C. |
| Sample 1-1 | Sodium polyoxybutylene (Mw = 700) propylenesulfonate | ◯ | ◯ | ◯ |
| Sample 1-2 | Sodium polyoxybutylene (Mw = 700) acetate | ◯ | ◯ | ◯ |
| Sample 1-3 | Sodium polyoxybutylene (Mw = 700) sulfated at one terminal | ◯ | ◯ | ◯ |
| Sample 1-4 | Sodium polyoxybutylene (Mw = 2000) sulfated at one terminal | ◯ | ◯ | ◯ |
| Sample 1-5 | Sodium polyoxybutylene (Mw = 2000) sulfated at both terminals | ◯ | ◯ | ◯ |
| Sample 1-6 | Sodium polyoxypropylene (Mw = 1000) | ◯ | Δ | ◯ |

TABLE 2-continued

|  | Emulsifier | 30 minutes ambient temperature | 3 days ambient temperature | −5° C. |
|---|---|---|---|---|
| Comparative Examples 1-1 | sulfated at one terminal Dodecyl sodium sulfate | ○ | ○ | X |
| Comparative Examples 1-2 | Sodium lauroyl-glutamate | ○ | ○ | X |
| Comparative Examples 1-3 | Sodium polyoxypropylene (Mw = 200) sulfated at one terminal | X | X | X |

As shown in Table 2, in Examples 1-1 to 1-6, in which a compound obtained by substituting sodium propylene-sulfonate, sodium acetate, or sodium sulfate on polyoxybutylene or polyoxypropylene having molecular weights of 700 to 2000 was used, the emulsification ability and the stability on standing, especially the emulsion stability at low temperature, were found to be excellent. Especially in Examples 1-1 to 1-5, in which polyoxybutylene was used, excellent emulsion stability was observed under all conditions. Thus, polyoxybutylene substitution compounds are considered more preferable. On the other hand, in Comparative Examples 1-1 and 1-2, in which a widely used emulsifier, sodium dodecyl sulfate or sodium lauroyl glutamate, was used, the emulsifier separated out under the storage at low temperature, and the separation of oil took place though a uniform milky white emulsion could be prepared. In addition, in Comparative Example 1-3, in which a sulfate ester of polyoxypropylene with a molecular weight of 200 (the average addition mole number of oxypropylenes is about 3.1) was used, the separation of oil was observed immediately after emulsification mixing, and the stable emulsion could not be prepared.

Then, the present inventors have evaluated the skin external preparations of the blending compositions shown in Table 3. In those blending compositions, various polyoxyalkylene substitution compounds are used as the emulsifier. The evaluation results are also shown in Table 3. The various evaluation items are as follows.

The appearance of emulsion was visually observed after being allowed to stand for 3 days at 25° C. The evaluation criteria were as follows.

○ . . . The emulsion was uniform and milky white.
Δ . . . A small amount of floating oil was observed; however, it was milky white.
X . . . Solid matter was observed, or the separation of the water phase and the oil phase was observed.

"Feeling in Use (1): Non-Sticky Feeling After Application"

The actual usage test by 10 professional panelists was conducted for the presence or absence of a sticky feeling after application. The evaluation criteria were as follows.

⊚ . . . 8 or more professional panelists recognized that there was no stickiness after application.
○ . . . 6 or more and less than 8 professional panelists recognized that there was no stickiness after application.
Δ . . . 3 or more and less than 6 professional panelists recognized that there was no stickiness after application.
X . . . less than 3 professional panelists recognized that there was no stickiness after application.

"Feeling in Use (2): Moist Feeling After Application"

The actual usage test by 10 professional panelists was conducted for the presence or absence of moist feeling after application. The evaluation criteria were as follows.

⊚ . . . 8 or more professional panelists recognized that there was a moist feeling after application.
○ . . . 6 or more and less than 8 professional panelists recognized that there was a moist feeling after application.
Δ . . . 3 or more and less than 6 professional panelists recognized that there was a moist feeling after application.
X . . . less than 3 professional panelists recognized that there was a moist feeling after application.

TABLE 3

| Blending components | Sample | | | | Comparative Examples | | | |
|---|---|---|---|---|---|---|---|---|
|  | 1-7 | 1-8 | 1-9 | 1-10 | 1-7 | 1-8 | 1-9 | 1-10 |
| Sodium polyoxybutylene (Mw = 700) sulfated at one terminal | 2 | — | — | — | — | — | — | 12 |
| Sodium polyoxybutylene (Mw = 2000) sulfated at one terminal | — | 2 | — | — | — | — | — | — |
| Sodium polyoxybutylene (Mw = 2000) sulfated at both terminals | — | — | 2 | — | — | — | — | — |
| Dodecyl sodium sulfate | — | — | — | — | 2 | — | — | — |
| Sodium lauroyl-glutamate | — | — | — | — | — | 2 | — | — |
| Sodium polyoxypropylene (Mw = 200) sulfated at one terminal | — | — | — | — | — | — | 2 | — |
| 1,3-Butylene glycol | 5 | 5 | 5 | 5 | 5 | 5 | 5 | 5 |
| Glycerin | 5 | 5 | 5 | 5 | 5 | 5 | 5 | 5 |
| Liquid paraffin | 3 | 3 | 3 | 3 | 3 | 3 | 3 | 3 |

TABLE 3-continued

|  | Sample | | | | Comparative Examples | | | |
| --- | --- | --- | --- | --- | --- | --- | --- | --- |
| Blending components | 1-7 | 1-8 | 1-9 | 1-10 | 1-7 | 1-8 | 1-9 | 1-10 |
| Cetyl octanoate | 4 | 4 | 4 | 4 | 4 | 4 | 4 | 4 |
| Stearyl alcohol | 0.5 | 0.5 | 0.5 | 0.5 | 0.5 | 0.5 | 0.5 | 0.5 |
| Xanthan gum | 0.3 | 0.3 | 0.3 | 0.3 | 0.3 | 0.3 | 0.3 | 0.3 |
| Antiseptic | proper quantity | proper quantity | proper quantity | proper quantity | proper quantity | proper quantity | proper quantity | proper quantity |
| Purified water | reminder | reminder | reminder | reminder | reminder | reminder | reminder | reminder |
| Emulsion stability | ○ | ○ | ○ | ○ | ○ | ○ | X | ○ |
| Feeling in use (1): Non-sticky feeling after application | ⊚ | ⊚ | ⊚ | ⊚ | X | Δ | ○ | Δ |
| Feeling in use (2): Moist feeling after application | ⊚ | ⊚ | ⊚ | ⊚ | ○ | Δ | Δ | ⊚ |

As shown in Table 3, the skin external preparations of Examples 1-7 to 1-10, in which the emulsifier of the present invention was blended, generated no sticky feeling, and a moist feeling was recognized in addition to good emulsion stability, and the texture in use was excellent. On the other hand, in Comparative Example 1-4, in which sodium dodecyl sulfate was blended, a sticky feeling was generated though there was a moist feeling. In Comparative Example 1-5, in which sodium lauroyl glutamate was blended, the texture in use was not satisfactory though the emulsion stability was high. In Comparative Example 1-6, in which a sulfate ester of polyoxypropylene with a molecular weight of 200 (the average addition mole number of oxypropylenes is about 3.1) was blended, the emulsion stability was especially poor. Furthermore, in Comparative Example 1-7, in which 12% sodium salt of polyoxybutylene (MW=700) sulfated at one terminal, of the present invention, was blended, the blending quantity was too high and a slight sticky feeling was recognized though the emulsion stability and the moist feeling were excellent.

In the following section, the examples of formulations for the skin external composition of the present invention are listed. However, the technical scope of the present invention is not limited by these. All the obtained compositions were excellent in emulsion stability and texture in use.

EXAMPLE 1-11

Emulsion

| (Blending composition) | (% by weight) |
| --- | --- |
| Dimethylpolysiloxane | 2.0 |
| Behenyl alcohol | 1.0 |
| Batyl alcohol | 0.5 |
| Glycerin | 5.0 |
| 1,3-butylene glycol | 7.0 |
| Sodium polyoxybutylene (Mw = 700) propanesulfonate | 2.0 |
| Hydrogenated oil | 3.0 |
| Squalane | 6.0 |
| Pentaerythritol tetra-2-ethylhexanoate | 2.0 |
| Succinoglycan | 0.3 |
| Antiseptic | proper quantity |
| Perfume | proper quantity |
| Purified water | remainder |

EXAMPLE 1-12

Cream

| (Blending composition) | (% by weight) |
| --- | --- |
| Liquid paraffin | 8.0 |
| Petrolatum | 3.0 |
| Dimethylpolysiloxane | 2.0 |
| Stearyl alcohol | 3.0 |
| Behenyl alcohol | 2.0 |
| Glycerin | 5.0 |
| Dipropylene glycol | 4.0 |
| Pentaerythritol tetra-2-ethylhexanoate | 4.0 |
| Polyoxyethylene glyceryl monoisostearate | 1.0 |
| Polyoxyethylene glyceryl monostearate | 1.0 |
| Lipophilic glyceryl monostearate | 2.0 |
| Sodium polyoxypropylene (Mw = 2000) sulfated at one terminal | 1.0 |
| Tocopheryl acetate | 0.1 |
| Trisodium edetate | 0.1 |
| Antiseptic | proper quantity |
| Purified water | remainder |
| Perfume | proper quantity |

EXAMPLE 1-13

Daytime Use Protector

| (Blending composition) | (% by weight) |
| --- | --- |
| Decamethylcyclopentasiloxane | 3.0 |
| Methylphenyl polysiloxane | 3.0 |
| Behenyl alcohol | 1.0 |
| 1,3-butylene glycol | 5.0 |
| Sodium polyoxybutylene (Mw = 700) sulfated at one terminal | 2.5 |
| Dipotassium glycyrrhizinate | 0.05 |
| Trimethylglycine | 1.0 |
| L-Ascorbic Acid 2-glucoside | 2.0 |
| Trisodium edetate | 0.1 |
| 2-Ethylhexyl p-methoxycinnamate | 7.0 |
| Xanthan gum | 0.1 |
| Carboxyvinylpolymer | 0.3 |
| Antiseptic | proper quantity |
| Purified water | remainder |
| Perfume | proper quantity |

EXAMPLE 1-14

Emulsified Foundation

| (Blending composition) | (% by weight) |
|---|---|
| Talc | 3.0 |
| Titanium dioxide | 5.0 |
| Red Iron Oxide | 0.5 |
| Yellow Iron Oxide | 1.4 |
| Black Iron Oxide | 0.1 |
| Bentonite | 1.0 |
| Dipropylene glycol | 10.0 |
| Stearic acid | 1.0 |
| Isostearic acid | 1.0 |
| Behenic acid | 1.0 |
| α-Oligomer | 10.0 |
| Cetyl 2-ethyl hexanoate | 2.0 |
| Behenyl alcohol | 0.5 |
| Batyl alcohol | 0.5 |
| Polyoxyethylene glyceryl monoisostearate | 2.0 |
| Glyceryl monostearate, selfemulsifying | 0.5 |
| Sodium polyoxybutylene (Mw = 2000) sulfated at one terminal | 1.0 |
| Potassium hydrate | 0.2 |
| Antiseptic | proper quantity |
| Perfume | proper quantity |
| Purified water | remainder |

Then, the present inventors have prepared various polyoxyalkylene substitution compounds according to the respective synthesis examples and evaluated the cleansers of the blending compositions shown in Table 4. The evaluation results are also shown in Table 4. The various evaluation items are as follows.

"Evaluation (1): Cleansing Power"

With artificial hard water of $CaCl_2/MgCl_2=3/1$ and 5° DH, 3% sample solution was prepared. An artificially sebum/dirt soiled cloth of wool serge was washed at 40° C. with a Tergoto Meter (JIS K-3371), and the rate of cleansing was determined by the following equation.

Rate of cleansing (%)={[Rs]−[Rd]/[Rs]−[Rc]}100

In the above-described formula, [Rc]: reflectivity of rubber before dirt application (control), [Rs]: reflectivity of rubber after dirt application (before cleansing operation), and [Rd]: reflectivity of rubber after cleansing operation.

The evaluation criteria for the "cleansing power" were as follows.

○ . . . good cleansing properties (rate of cleansing: 70% or higher)

Δ . . . average cleansing properties (rate of cleansing: 50% or higher and lower than 70%)

X . . . poor cleansing properties (rate of cleansing: lower than 50%)

"Evaluation (2): Non-Sticky Feeling After Cleansing"

The actual usage test by 10 professional panelists was conducted for the presence or absence of a sticky feeling after cleansing. The evaluation criteria were as follows.

⊚ . . . 8 or more professional panelists recognized that there was no stickiness after cleansing.

○ . . . 6 or more and less than 8 professional panelists recognized that there was no stickiness after cleansing.

Δ . . . 3 or more and less than 6 professional panelists recognized that there was no stickiness after cleansing.

X . . . less than 3 professional panelists recognized that there was no stickiness after cleansing.

"Evaluation (3): Moist Feeling After Cleansing"

The actual usage test by 10 professional panelists was conducted for the presence or absence of moist feeling after cleansing. The evaluation criteria were as follows.

⊚ . . . 8 or more professional panelists recognized that there was a moist feeling after cleansing.

○ . . . 6 or more and less than 8 professional panelists recognized that there was a moist feeling after cleansing.

Δ . . . 3 or more and less than 6 professional panelists recognized that there was a moist feeling after cleansing.

X . . . less than 3 professional panelists recognized that there was a moist feeling after cleansing.

"Evaluation (4): Skin Irritation Test"

A 24-hour occlusive patch test was performed on the medial side of the upper arm of 10 panelists, and the average value was calculated based on the following criteria.

0 . . . No abnormality was observed.
1 . . . Slight redness was observed.
2 . . . Redness was observed.
3 . . . Redness and papules were observed.

The evaluation criteria for the "skin irritation test" were as follows.

○ . . . Average value of 10 panelists: lower than 0.2
Δ . . . Average value of 10 panelists: 0.2 or higher and lower than 0.3
X . . . Average value of 10 panelists: 0.3 or higher

TABLE 4

| Blending components | Sample | | | | | Comparative Examples | | |
|---|---|---|---|---|---|---|---|---|
| | 2-1 | 2-2 | 2-3 | 2-4 | 2-5 | 2-1 | 2-2 | 2-3 |
| Sodium polyoxybutylene (Mw = 700) propylenesulfonate | 20 | — | — | — | — | — | — | — |
| Sodium polyoxybutylene (Mw = 700) acetate | — | 20 | — | — | — | — | — | — |
| Sodium polyoxybutylene (Mw = 700) sulfated at one terminal | — | — | 20 | — | — | — | — | — |
| Sodium polyoxybutylene (Mw = 2000) sulfated at both terminals | — | — | — | 20 | — | — | — | — |
| Sodium polyoxypropylene (Mw = 1000) sulfated at both terminals | — | — | — | — | 20 | — | — | — |

TABLE 4-continued

|  | Sample | | | | | Comparative Examples | | |
|---|---|---|---|---|---|---|---|---|
| Blending components | 2-1 | 2-2 | 2-3 | 2-4 | 2-5 | 2-1 | 2-2 | 2-3 |
| Dodecyl sodium sulfate | — | — | — | — | — | 20 | — | — |
| Sodium lauroyl-glutamate | — | — | — | — | — | — | 20 | — |
| Sodium polyoxypropylene (Mw = 200) sulfated at one terminal | — | — | — | — | — | — | — | 20 |
| 1,3-Butylene glycol | 2 | 2 | 2 | 2 | 2 | 2 | 2 | 2 |
| Solbitol solution | 10 | 10 | 10 | 10 | 10 | 10 | 10 | 10 |
| Antiseptic | proper quantity | proper quantity | proper quantity | proper quantity | proper quantity | proper quantity | proper quantity | proper quantity |
| Perfume | proper quantity | proper quantity | proper quantity | proper quantity | proper quantity | proper quantity | proper quantity | proper quantity |
| Purified water | reminder | reminder | reminder | reminder | reminder | reminder | reminder | reminder |
| Evaluation (1): Cleansing power | ○ | ○ | ○ | ○ | Δ | ○ | ○ | X |
| Evaluation (2): Non-sticky feeling after cleansing | ◎ | ◎ | ◎ | ◎ | ○ | X | Δ | Δ |
| Evaluation (3): Moist feeling after cleansing | ◎ | ◎ | ◎ | ◎ | ○ | ○ | Δ | Δ |
| Evaluation (4): Skin irritation test | ○ | ○ | ○ | ○ | ○ | Δ | Δ | Δ |

As shown in Table 4, in Examples 2-1 to 2-5, in which a compound obtained by substituting sodium propylenesulfonate, sodium acetate, or sodium sulfate on polyoxybutylene or polyoxypropylene having molecular weights of 700 to 2000 was blended, cleanser compositions excellent in texture in use and having low skin irritation could be obtained. Especially in Examples 2-1 to 2-4, in which polyoxybutylene was used, the cleansing power was excellent. Thus, polyoxybutylene substitution compounds are considered more preferable. On the other hand, in Comparative Example 2-1, in which a widely used cleanser, sodium dodecyl sulfate, was used, there was a sticky feeling and the skin irritation property was not desirable though the cleansing power was high. In addition, in Comparative Example 2-2, in which sodium lauroyl glutamate was used, the texture in use and the skin irritation property were not satisfactory. Furthermore, in Comparative Example 2-3, in which a sulfate ester of polyoxypropylene with a molecular weight of 200 (the average addition mole number of oxypropylenes is about 3.1) was used, the cleansing power was especially poor.

In order to investigate the optimum blending quantity of the cleanser of the present invention, the cleanser evaluation was conducted, in the same way as the above-described test examples, using the blending compositions shown in Table 5. The evaluation results are also shown in Table 5.

TABLE 5

|  | Sample | | | |
|---|---|---|---|---|
| Blending components | 2-6 | 2-7 | 2-8 | 2-9 |
| Sodium polyoxybutylene (Mw= 700) sulfated at one terminal | 0.1 | 1 | 30 | 60 |
| 1,3-Butylene glycol | 2 | 2 | 2 | 2 |
| Solbitol solution | 10 | 10 | 10 | 10 |
| Antiseptic | proper quantity | proper quantity | proper quantity | proper quantity |
| Perfume | proper quantity | proper quantity | proper quantity | proper quantity |
| Purified water | reminder | reminder | reminder | reminder |
| Evaluation (1): Cleansing power | Δ | ○ | ○ | ○ |
| Evaluation (2): Non-sticky feeling after cleansing | ○ | ◎ | ◎ | ○ |
| Evaluation (3): Moist feeling after cleansing | ○ | ◎ | ◎ | ◎ |
| Evaluation (4): Skin irritation test | ○ | ○ | ○ | ○ |

As shown in Table 5, it was confirmed that the texture in use was excellent and the irritating property was low when the blending quantity of the cleanser of the present invention was in the range of 0.1 to 60 mass %. The cleansing power increased with an increase in the blending quantity, and excellent cleansing power was achieved especially at 1 mass % or higher.

In the following section, the examples of formulations for the cleanser composition of the present invention are listed. However, the technical scope of the present invention is not limited by these. All the obtained compositions were excellent in cleansing power and texture in use and had low skin irritation.

EXAMPLE 2-10

Body Shampoo

| (Blending composition) | (% by weight) |
|---|---|
| Hydroxypropyl methylcellulose | 0.1 |
| Glycerin | 8.0 |
| Dipropylene glycol | 5.0 |
| Triethanolamine laurate | 12.0 |

-continued

| (Blending composition) | (% by weight) |
|---|---|
| Lauryl dimethylaminoacetic acid betaine | 5.0 |
| Coconut fatty acid diethanolamide | 3.0 |
| Sodium polyoxybutylene (Mw = 700) sulfated at one terminal | 5.0 |
| Chamomile extract | proper quantity |
| Trisodium edetate | proper quantity |
| Antiseptic | proper quantity |
| Coloring material | proper quantity |
| Perfume | proper quantity |
| Purified water | remainder |

EXAMPLE 2-11

Cleasing Form

| (Blending composition) | (% by weight) |
|---|---|
| Glycerin | 25.0 |
| Solbitol solution (70%) | 5.0 |
| Polyethylene glycol 1500 | 10.0 |
| Stearic acid | 9.0 |
| Lauric acid | 4.0 |
| Myristic acid | 10.0 |
| Polyoxyethylene glyceryl isostearate | 2.0 |
| Glyceryl monostearate, selfemulsifying | 2.0 |
| Lauryl dimethylaminoacetic acid betaine | 1.0 |
| Sodium polyoxybutylene (Mw = 700) propanesulfonate | 5.0 |
| Talc | 0.1 |
| Potassium hydrate | 4.0 |
| Balm mint extract | 0.1 |
| Trisodium edetate | proper quantity |
| Ethylcellulose | proper quantity |
| Perfume | proper quantity |
| Purified water | remainder |

What is claimed is:

1. A surfactant consisting of a compound represented by the below-described general formula (1):

$$Y\text{—}O\text{-}(EO)_l\text{-}(AO)_m\text{-}(EO)_n\text{-}X \tag{1}$$

wherein AO represents an oxyalkylene group having 3 to 4 carbon atoms; m is the average addition mole number of the oxyalkylene group and satisfies $5 \leq m \leq 100$; EO represents an oxyethylene group; l and n are the average addition mole numbers of the oxyethylene groups and satisfy $l=n=0$; either X or Y or both are a functional group represented by —SO$_3$M, —COOM, —HPO$_3$M, or —(CH$_2$)$_q$—COOM, wherein M is a hydrogen ion or a monovalent inorganic or organic cation, and q is the number of carbon atoms of the linked alkylene group and satisfies $1 \leq q \leq 4$; when either X or Y is the above-described functional group, the other one can be a hydrogen atom, a methyl group, or an ethyl group; the percentage of oxyalkylene groups having 4 carbon atoms with respect to the sum of AO is 50 mass % or higher.

2. An emulsifier consisting of the surfactant according to claim 1.

3. A skin external composition comprising one or more emulsifiers represented by the below-described general formula (1):

$$Y\text{—}O\text{-}(EO)_l\text{-}(AO)_m\text{-}(EO)_n\text{-}X \tag{1}$$

wherein AO represents an oxyalkylene group having 3 to 4 carbon atoms; m is the average addition mole number of the oxyalkylene group and satisfies $5 \leq m \leq 100$; EO represents an oxyethylene group; l and n are the average addition mole numbers of the oxyethylene groups and satisfy $l=n=0$; either X or Y or both are a functional group represented by —SO$_3$M, —COOM, —HPO$_3$M, or —(CH$_2$)$_q$—COOM, wherein M is a hydrogen ion or a monovalent inorganic or organic cation, and q is the number of carbon atoms of the linked alkylene group and satisfies $1 \leq q \leq 4$; when either X or Y is the above-described functional group, the other one can be a hydrogen atom, a methyl group, or an ethyl group; the percentage of oxyalkylene groups having 4 carbon atoms with respect to the sum of AO is 50 mass % or higher.

4. A skin external composition according to claim 3, comprising 0.001 to 10 mass % of the said emulsifier.

5. A cleanser consisting of the surfactant according to claim 1.

6. A cleanser composition comprising one or more cleansers represented by the below-described general formula (1):

$$Y\text{—}O\text{-}(EO)_l\text{-}(AO)_m\text{-}(EO)_n\text{-}X \tag{1}$$

wherein AO represents an oxyalkylene group having 3 to 4 carbon atoms; m is the average addition mole number of the oxyalkylene group and satisfies $5 \leq m 100$; EO represents an oxyethylene group; l and n are the average addition mole numbers of the oxyethylene groups and satisfy $l=n=0$; either X or Y or both are a functional group represented by —SO$_3$M, —COOM, —HPO$_3$M, or —(CH$_2$)$_q$—COOM, wherein M is a hydrogen ion or a monovalent inorganic or organic cation, and q is the number of carbon atoms of the linked alkylene group and satisfies $1 \leq q \leq 4$; when either X or Y is the above-described functional group, the other one can be a hydrogen atom, a methyl group, or an ethyl group; the percentage of oxyalkylene groups having 4 carbon atoms with respect to the sum of AO is 50 mass % or higher.

7. A cleanser composition according to claim 6, comprising 0.1 to 60 mass % of the said cleanser composition.

* * * * *